US009031634B2

(12) United States Patent
Flask et al.

(10) Patent No.: US 9,031,634 B2
(45) Date of Patent: May 12, 2015

(54) CHEMICAL SHIFT MARKERS FOR IMPROVED WIRELESS FIDUCIAL MARKER TRACKING

(76) Inventors: Christopher Flask, Avon Lake, OH (US); Jonathan Lewin, Beachwood, OH (US); Daniel Elgort, Cleveland Heights, OH (US); Ken Pin Wang, Houston, TX (US); Eddy Wong, Cleveland Heights, OH (US); Jeffrey Duerk, Avon Lake, OH (US)

( * ) Notice: Subject to any disclaimer, the term of this patent is extended or adjusted under 35 U.S.C. 154(b) by 3368 days.

(21) Appl. No.: 10/514,307

(22) PCT Filed: May 15, 2003

(86) PCT No.: PCT/US03/15240
§ 371 (c)(1),
(2), (4) Date: Jan. 4, 2008

(87) PCT Pub. No.: WO03/098232
PCT Pub. Date: Nov. 27, 2003

(65) Prior Publication Data
US 2008/0221428 A1    Sep. 11, 2008

Related U.S. Application Data

(60) Provisional application No. 60/381,489, filed on May 17, 2002.

(51) Int. Cl.
*A61B 5/055*    (2006.01)
*G01R 33/28*    (2006.01)
*A61B 19/00*    (2006.01)
*A61B 5/06*    (2006.01)

(52) U.S. Cl.
CPC ............... *G01R 33/285* (2013.01); *A61B 19/54* (2013.01); *A61B 2019/5454* (2013.01); *A61B 5/055* (2013.01); *A61B 5/06* (2013.01)

(58) Field of Classification Search
CPC .................. A61B 5/055; A61B 19/54; A61B 2019/5454; A61B 5/06; G01R 33/285
USPC .................. 600/407, 410, 409; 324/307, 309
See application file for complete search history.

(56) References Cited

U.S. PATENT DOCUMENTS 4,792,758 A * 12/1988 Sattin ............................ 324/309
5,462,725 A    10/1995 Kiefer et al.
(Continued)

OTHER PUBLICATIONS

International Search Report for International Application No. PCT/US03/15240, Jun. 16, 2005.

*Primary Examiner* — Vani Gupta

(57) ABSTRACT

A new and improved method for tracking and/or spatial localization of an invasive device in Magnetic Resonance Imaging (MRI) is provided. The invention includes providing an invasive device including a marker having a chemically shifted signal source with a resonant frequency different from the chemical species of the subject to be imaged, applying a pulse sequence, detecting the resulting RF magnetic resonance signals, and determining the 3D coordinates of the marker. The invention also includes generating scan planes and reconstructing an image from the detected signals to generate an image having the marker contrasted from the subject. The invasive device includes a marker having a chemically shifted signal source which has a resonant frequency different from the chemical species of the subject to be imaged for use in tracking the device during imaging.

26 Claims, 9 Drawing Sheets

(56) References Cited

U.S. PATENT DOCUMENTS

| | | |
|---|---|---|
| 5,498,421 A | 3/1996 | Grinstaff et al. |
| 5,545,993 A | 8/1996 | Taguchi et al. |
| 5,726,569 A * | 3/1998 | Krieg et al. ............ 324/309 |
| 6,181,134 B1 * | 1/2001 | Wald ...................... 324/307 |
| 6,574,497 B1 * | 6/2003 | Pacetti .................... 600/420 |
| 7,037,416 B2 * | 5/2006 | Parce et al. .............. 204/451 |

* cited by examiner

| XY | | YZ | | XYZ |
|---|---|---|---|---|
| (-100, 15) | | (-10, 65) | → | (45, -10, 65) |
| (25, 75) | | (15, 35) | → | (-100, 15, 35) |
| (45, -10) | | (75, -95) | → | (25, 75, -95) |

CHEMICAL SHIFT MARKERS FOR IMPROVED WIRELESS FIDUCIAL MARKER TRACKING

BACKGROUND OF THE INVENTION

The present invention relates to a system and method for spatial localization of an invasive device in Magnetic Resonance Imaging (MRI). More particularly, the invention relates to a system and method for tracking an invasive device during MRI imaging.

MRI provides visual information about the interior of a subject which can be very useful for surgical procedures. Using MRI, surgical tools such as interventional devices, also known as invasive devices, can be used to minimize the size of incisions resulting in shorter recovery times. The use of small incisions requires the invasive devices to be guided or tracked since they cannot be directly observed within the subject. MR-guided device tracking has generated considerable interest as a result.

One key component of current tracking methods is the ability to automatically define an appropriate MRI imaging scan plane. Optical navigational systems have been developed to provide interactive scan plane selection by measuring the position of reflective materials mounted onto the surface of a rigid interventional device. Optical tracking systems have limitations including requiring a line-of-sight between the markers and the detection system. This hinders positioning of the detection systems within the scan room which in turn restricts the range-of-motion of the physician during the procedure. Also, these optical detection systems add additional, and potentially expensive, components to an already congested physical environment and they require calibration between the tracking system and the MRI coordinate frames.

An improved wireless tracking method was recently developed using inductively coupled tuned fiducial markers, a limited projection reconstruction sequence (LPR-FISP), and a fast localization algorithm to provide automatic scan plane selection for interventional procedures. This tracking method improved upon optical tracking systems by providing fast, automatic scan plane selection without a line-of-sight requirement between the markers and the detection system. Unfortunately, this system of fiducial marker contrast using tuned coils is dependent on the position and orientation of the marker coil with respect to the transmitter and receiver coils. In certain orientations, this dependence can result in attenuation of the marker signal and a loss of tracking function. It is desirable to provide a wireless tracking system and method to track markers which reduces the dependency of the signal strength on the position and/or orientation of the marker.

SUMMARY OF THE INVENTION

According to the present invention, a new and improved method for spatial localization of an invasive device in Magnetic Resonance Imaging (MRI) is provided.

In accordance with a first aspect of the invention, the invention includes providing an invasive device including a marker having a chemically shifted signal source with a resonant frequency different from the chemical species of the subject to be imaged, applying a pulse sequence, detecting the resulting RF magnetic resonance signals, determining the 3D coordinates of the marker.

In accordance with second aspect of the invention, the invention includes selecting scan planes for MR imaging.

In accordance with another aspect of the invention, the invention includes reconstructing an image from the detected signals to generate an image having the marker contrasted from the subject.

In accordance with a yet another aspect of the invention, an invasive device for use in Magnetic Resonance Imaging (MRI) of a subject is disclosed having a marker with a chemically shifted signal source which has a resonant frequency different from the chemical species of the subject to be imaged for use in tracking the device during imaging.

In accordance with a yet another aspect of the invention, a method for selecting a scan plane in MRI is provided. The method includes providing an invasive device including a marker having a chemically shifted signal source with a resonant frequency different from the chemical species of a subject to be imaged, applying a pulse sequence, detecting the resulting RF magnetic resonance signals, determining the 3D coordinates of the marker, and selecting a scan plane which include the 3D coordinates of the marker.

Other features, benefits and advantages of this invention will become apparent to those skilled in the art from the following detailed description of the preferred embodiments, when read in light of the accompanying drawings.

BRIEF DESCRIPTION OF THE DRAWINGS

The invention may take form in certain components and structures, preferred embodiments of which will be illustrated in the accompanying drawings wherein.

DETAILED DESCRIPTION OF THE INVENTION

Figure 1:
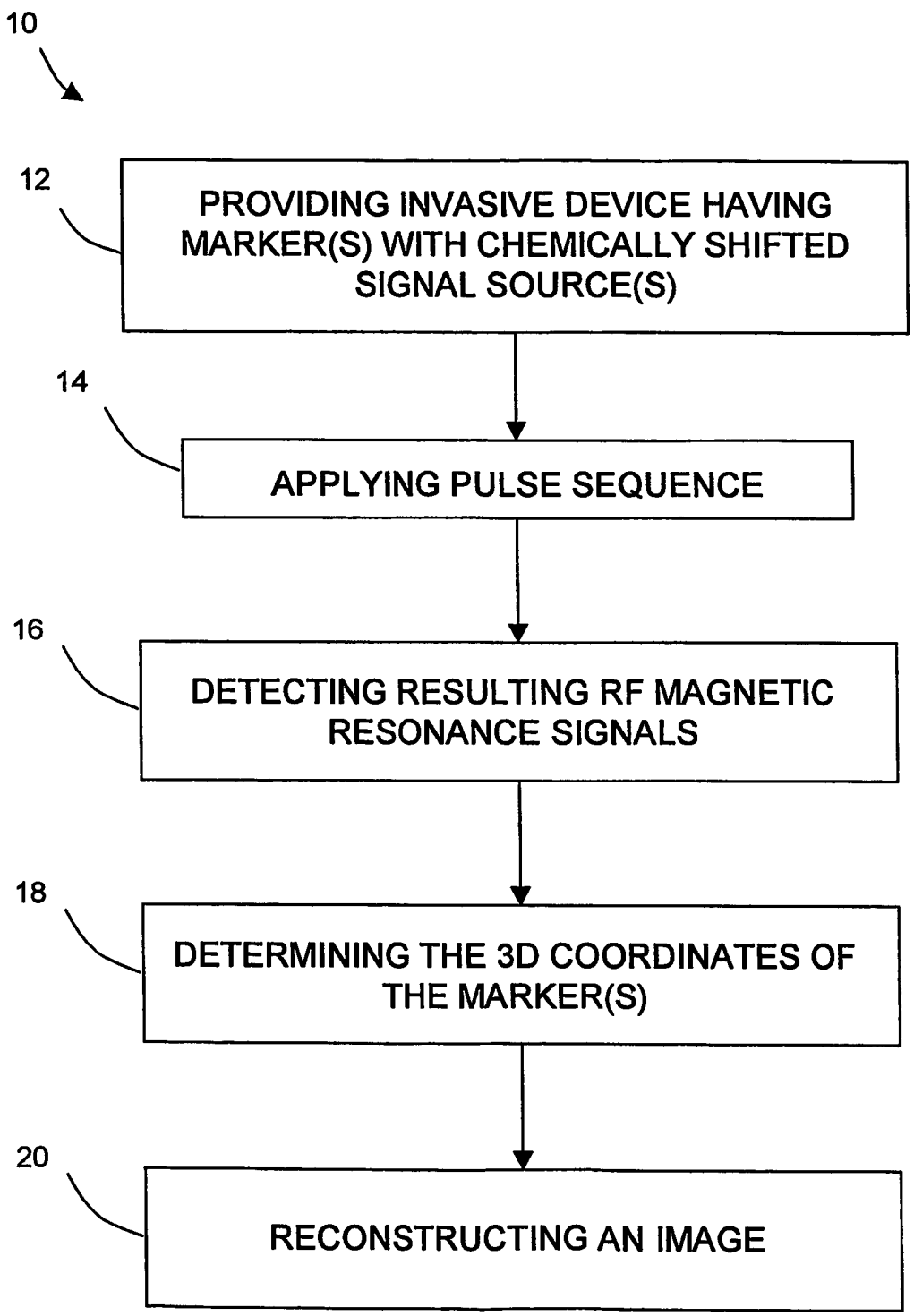
FIG. 1 illustrates a method of invasive device tracking in accordance with the invention.

Referring now to FIG. 1, a method for spatial localization of an invasive device in a subject using MRI is shown generally at 10. The method 10 includes providing an invasive device at 12 with a marker, also known as a fiducial marker, having a chemically shifted signal source which has a resonant frequency different from the chemical species of the subject to be imaged. The fiducial markers provide a set of highly localized signal sources that are tracked to determine the location and/or orientation of the invasive device.

Figure 2:
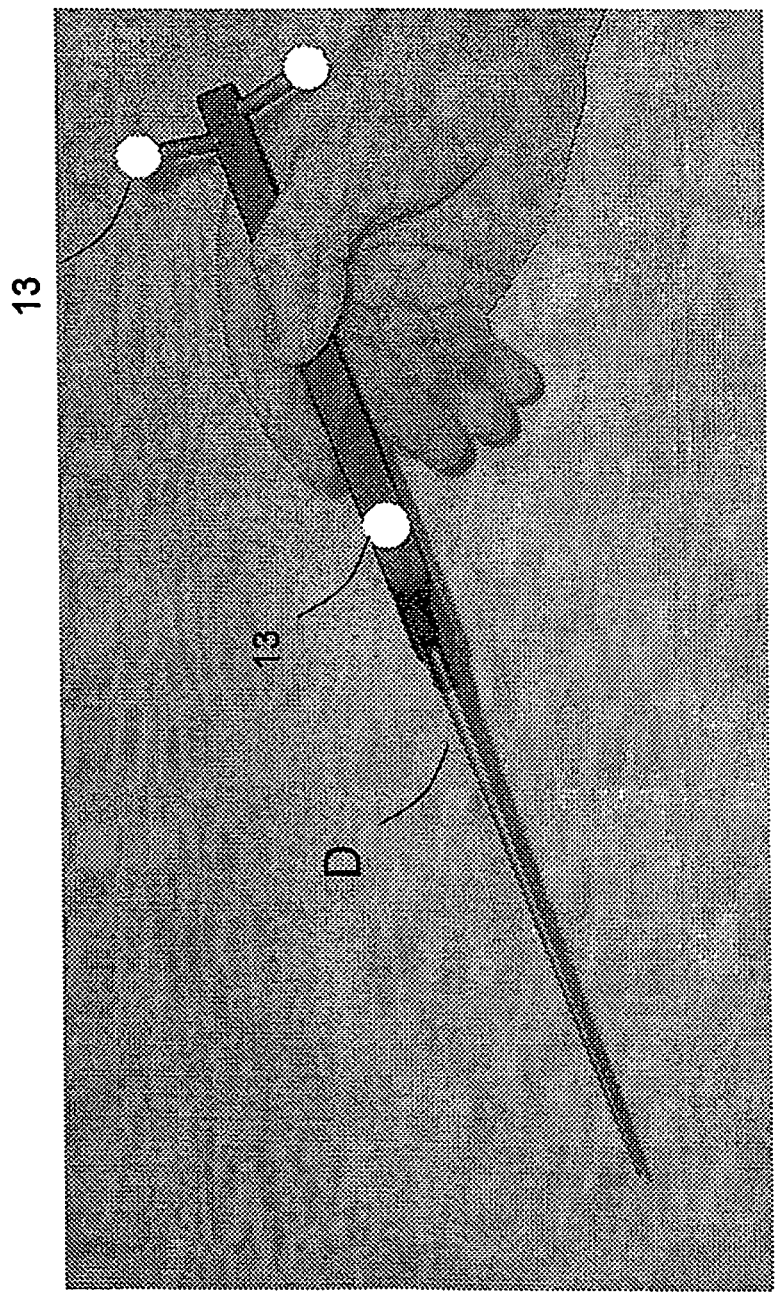
FIG. 2 is an illustration of an invasive device with markers attached thereto in accordance with the invention.

The invasive device can have one or a plurality of markers attached thereto, disposed either in, on, or about the device. Referring now to FIG. 2, an invasive device D is shown having three markers 13 attached to the outer surface of the device. The invasive device D can be a catheter, a guide wire, an endoscope, a laparoscope, a biopsy needle, a surgical instrument or any other suitable known interventional or invasive device.

The markers 13 each have a chemically shifted signal source with a resonant frequency different from the chemical species of the subject to be imaged (not shown). Markers were created by infusing 2.5 ml of concentrated acetic acid ($\sigma$~10 ppm)) doped with 1 mM Gd contrast (OPTIMARK™, Mallinckrodt Inc.) into 12 ml syringes (ID=15 mm) to provide a signal source with a proton chemical shift distinct from tissue protons encountered in a typical scanned volume. However, any suitable marker having any suitable amount of a chemically shifted signal source different from the chemical species of the subject to be imaged can be used. Other examples, which should not be considered limiting, can include blood-safe compounds including fluorinated compounds, such as perflourocarbon or any suitable known materials having a unique resonant frequency different from the chemical species of the subject to be imaged.

The one or more markers 13 can be disposed in any suitable known arrangement. The use of a known arrangement enables the one or more markers 13 to provide device location and/or orientation information. For example, the marker 13 can be arranged as a point source. A single marker 13 can be disposed at the tip of the device D to indicate the location of the device tip. The marker 13 can be arranged as a line source, with the line providing device orientation information. Several markers 13 can be used as points sources. The point sources can be arranged in a line, or three or more can be arranged to form a plane as shown in FIG. 2. The plane can provide useful device orientation information.

Referring again to FIG. 1, the method 10 further includes applying an MR pulse sequence to at least a portion of the subject at 14. A fast, radial MRI pulse sequence was used for detecting the local signal from the fiducial markers and suppressing other signals in the image volume.

Figure 3:
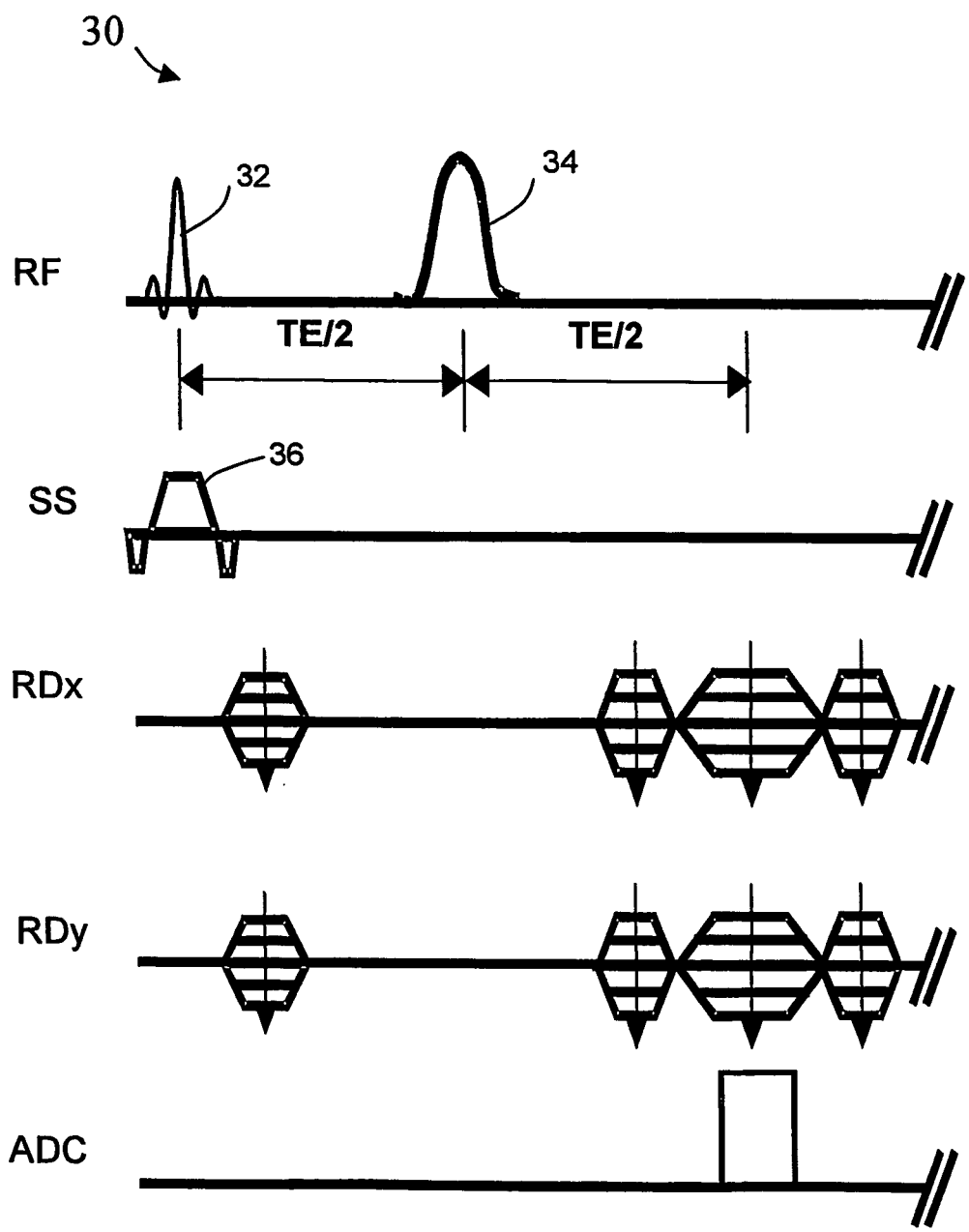
FIG. 3 is a radial 2-pulse missing pulse steady state sequence.

Referring to FIG. 3, a radial 2-pulse missing pulse steady state (MPSSFP) sequence (TR/TE/FA=30 ms/20 ms/135°) shown generally at 30 was used. The pulse sequence includes a slice-selective RF excitation pulse (TH=100 mm) shown at 32 and a chemical shift selective RF excitation pulse shown at 34 to generate marker-only projections. If scan volumes are used, the pulse 32 is a volume selective RF excitation pulse.

Dephasing as shown at 36 was applied in the readout direction following the slice-selective pulse 32 to remove residual signal from the subject. The slice-selective RF excitation 32 was used to prevent off-resonance spins at the edge of the main magnetic field from contributing to the marker-only images. Alternatively, any known pulse sequence suitable for device tracking can be used.

The method 10 further includes detecting the resulting RF magnetic resonance signals at 16. The signals are detected in any suitable manner. Scan planes containing the marker or markers 13 are acquired. The pulse sequence can generate a limited set of 1D projections that can be analyzed by the localization algorithm as described below. Ideally, the sequence would detect only projection information from the fiducial markers while suppressing signal from all other sources (e.g., patient or water phantom, here). Alternatively, scan volumes containing the marker or markers 13 can be acquired in any suitable known manner.

The method 10 further includes determining the 3D coordinates of the marker or markers at 18. A computer algorithm was used to analyze the 1D projections from the pulse sequence and to identify the 3D coordinates of the fiducial markers 13.

A five-stage method to accurately determine the 3D coordinates of the fiducial markers 13 was developed. However, this method is given for the purposes of example only and the 3D coordinates of the fiducial markers can be determined in any suitable known manner from the scan planes or scan volumes. In phase one, the algorithm converts the raw MRI projection data into the spatial domain, by applying a 1D-IFFT, and finds the location of the markers within each projection. In phase two, the algorithm analytically determines the location of all the intersections that would be created by backprojecting the marker signal peaks that were found in each projection into the scan plane. Phase three involves designating a subset of these intersection points as reference points and forming a "closest-point set" around each of these points. In phase four, the centroids of the N densest "closest-point sets" are used to represent the 2D locations of the fiducial markers in the scan plane (with N equal to the number of markers used, in this example N=3). Finally, in phase five, the 3D locations of the markers are calculated. The XY and YZ coordinates are found separately using the aforementioned method, and by matching the corresponding Y coordinates, 3D locations are assigned to each fiducial marker.

Figure 4:
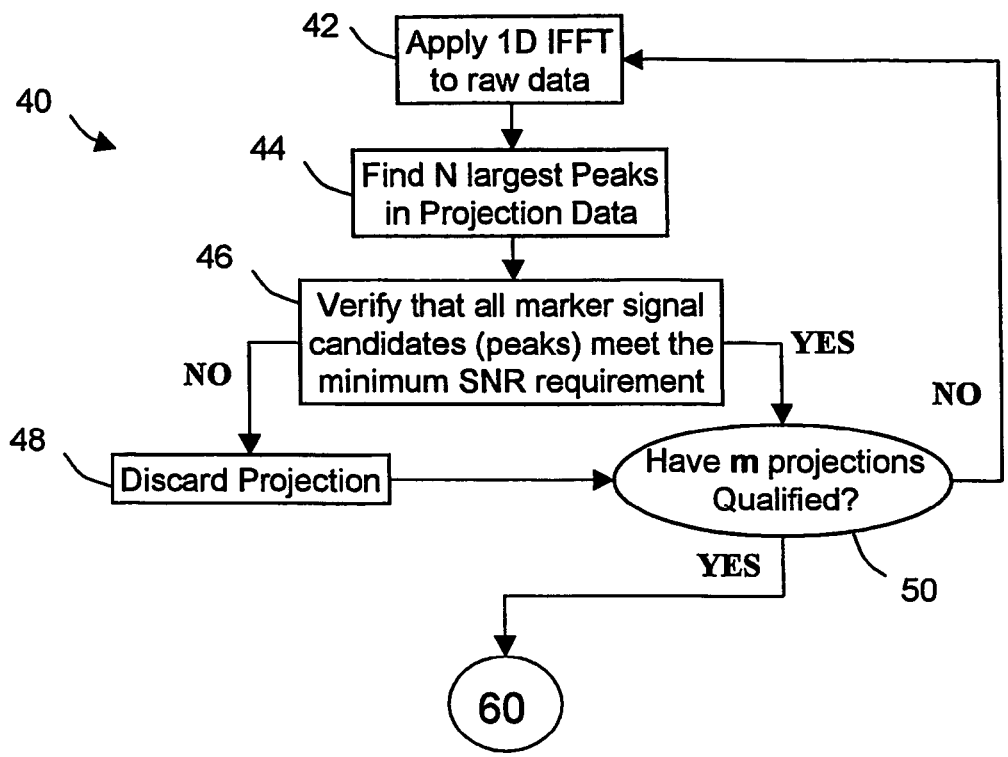
FIG. 4 illustrates steps of the invention.

Referring now to FIG. 4, the step of determining the 3D coordinates of fiducial markers 18 includes converting the raw MRI projection data into the spatial domain, by applying a 1D-IFFT, and finding the location of the markers within each projection shown generally at 40. The algorithm was designed to perform marker localization using a pre-determined number of projections in each scan plane (typically this value was set to 5, although any suitable number may be used). For a projection to be useful to the localization algorithm, all of markers signals should be identified within the projection. In this example, 3 markers were used, although any suitable number of markers can be used.

Figure 5:
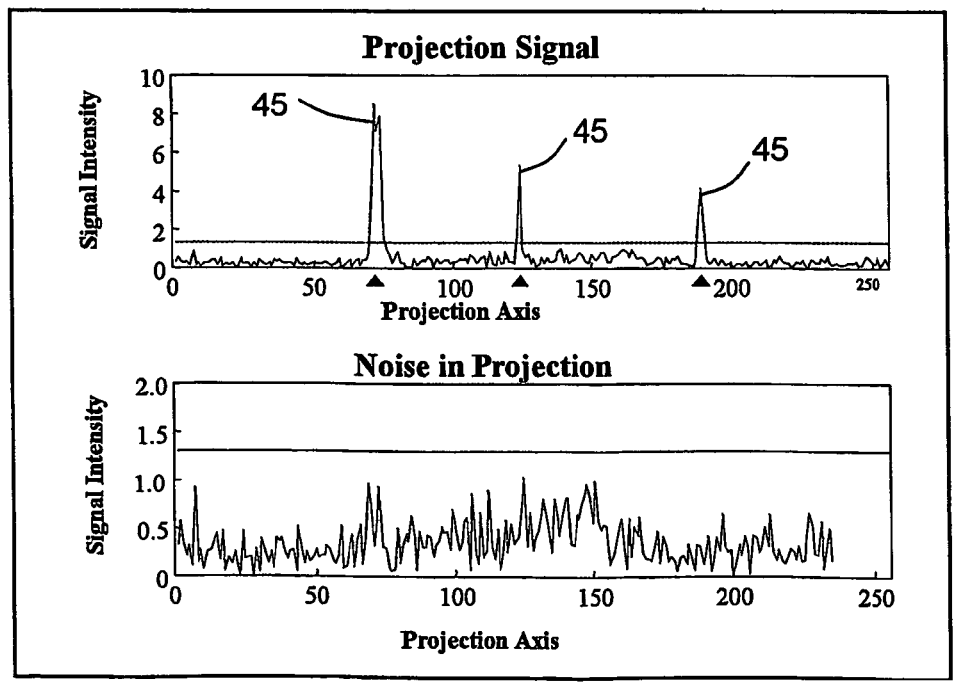
FIG. 5 illustrates projection signal peaks used in determining the 3D coordinates of the fiducial markers in accordance with the invention.

The raw MRI projection data was converted into the spatial domain by applying a 1D-IFFT at 42. Numerical algorithms were then used to search for fiducial marker signals in the projections by identifying the 3 largest signal peaks at 44. A discrete differentiation formula was used to identify the 3 largest local maxima in each projection. For the purposes of example, the 3 peaks in a projection are shown at 45 in FIG. 5.

Next it was verified that all of the peaks 45 met an experimentally determined minimum signal to noise ratio (SNR) threshold at 46. The SNR of each peak was then calculated by dividing the intensity of the signal peak by the mean background noise level in the projection. This noise level was estimated by removing all 3 marker signal candidates (which included the signal peaks and four data points on either side of each peak) from the projection data. If any of the 3 marker signal candidates did not meet the minimum SNR requirement, the entire projection was discarded at 48. This step was continued until enough satisfactory projections were identified at 50.

Figure 6:
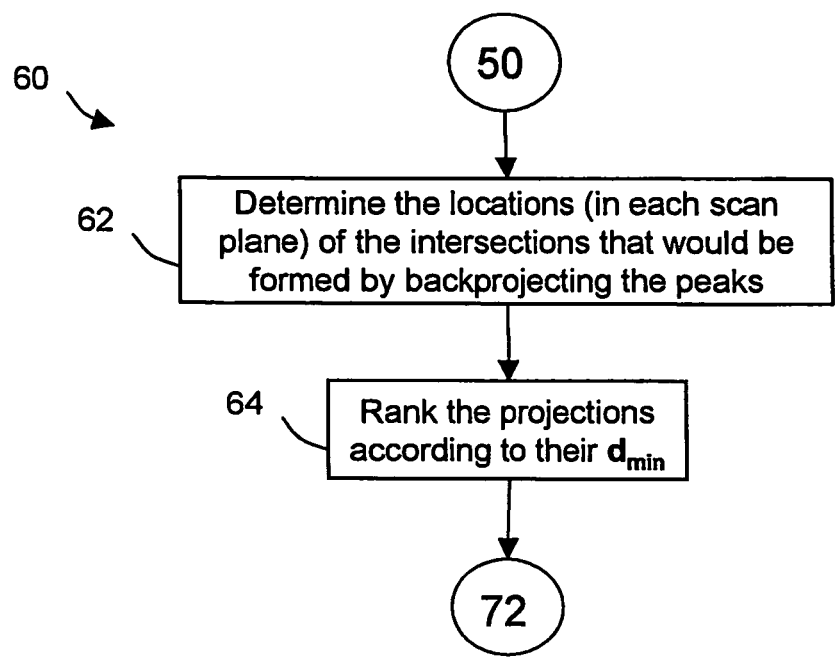
FIG. 6 illustrates steps of the invention.
Figure 7:
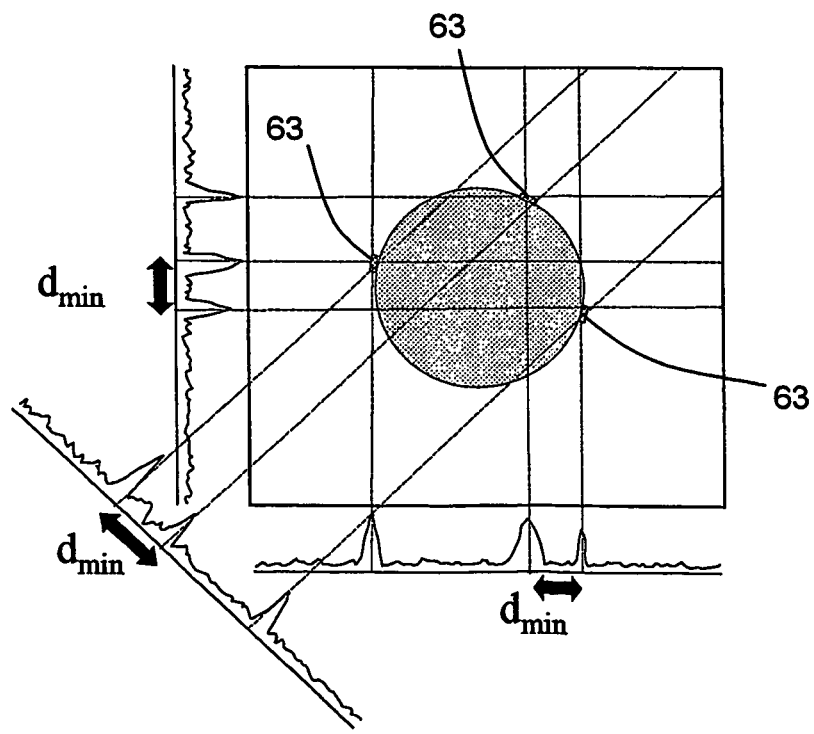
FIG. 7 illustrates the intersections created by backprojecting the marker signal peaks from each projection in accordance with the invention.

Referring now to FIG. 6, the step of determining the 3D coordinates of fiducial markers 13 also includes analytically calculating projection intersections as shown generally at 60. The algorithm determines at 62 the location of all the intersections 63 that would be created by backprojecting the marker signal peaks 45 from each projection as shown in FIG. 7.

This intersections were determined analytically by representing every marker signal peak 45 by a linear equation defined by a slope (tan θ) and an intercept (S/cos θ). Here θ is the projection angle and S is the location of the peak along the projection axis. The solution of any two linear equations (provided they do not correspond to marker signals from the same projection) defines an intersection point 63 in the scan plane. The linear equations from a pair of projections define $N^2$ intersection points, and N of these points corresponds to the location of a fiducial marker (with N=3 in this example). By solving for the intersections generated by every possible combination of projections, $$\binom{m}{2} * N^2$$

intersections were found in the scan plane. Here m is the number of projections used by the algorithm. The projections were ranked according to their $d_{min}$ as described below.

Figure 8:
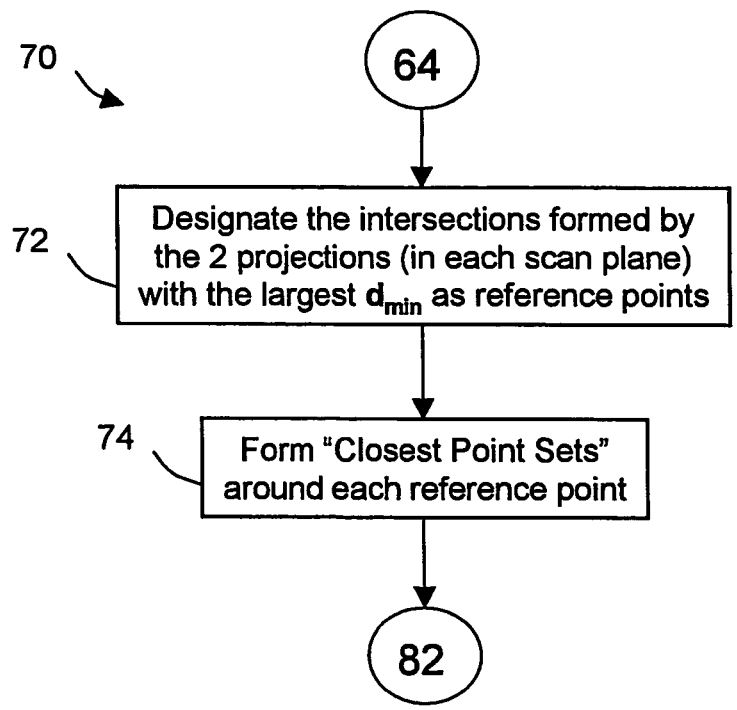
FIG. 8 illustrates steps of the invention.
Figure 9:
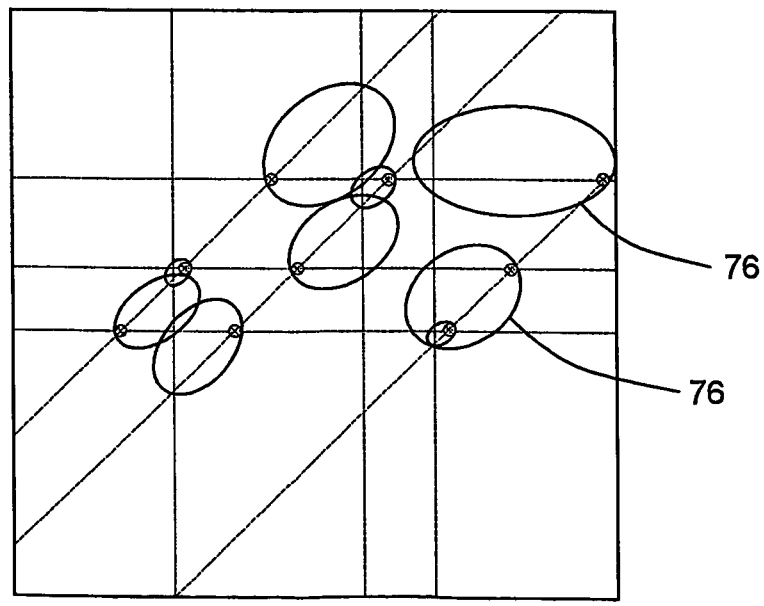
FIG. 9 illustrates closest-point sets used for determining the 3D coordinates of the fiducial markers in accordance with the invention.

Referring now to FIG. 8, the step of determining the 3D coordinates of fiducial markers also includes generating Reference Points and Closest-Point Sets shown generally at 70. Intersection points generated by some pair of projections were designated as reference points in the scan plane at 72. The two projections used to define the reference points were those that had the largest distance separating their two closest marker signal peaks 45, $d_{min}$ as shown in FIG. 7, to ensure that the reference points were well distributed in the scan plane and not too close together. A "closest-point set", shown as 76 in FIG. 9, containing the intersection point 63 from each of the $$\binom{m}{2}$$

projection pairs that was closest to the reference point, was formed around each reference point at 74. Closest-point sets were generated by iteratively searching through each set of intersection points and selecting the point that was geometrically closest to a given reference point.

Figure 10:
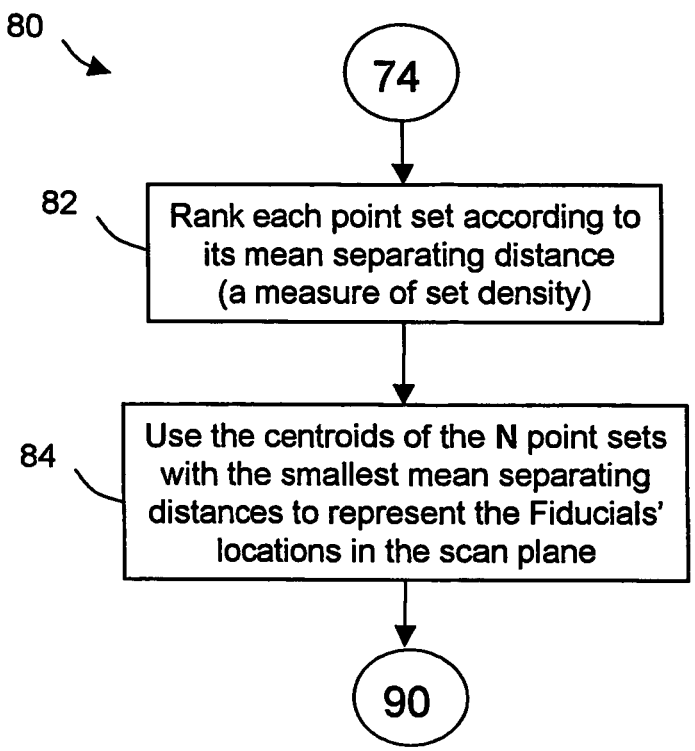
FIG. 10 illustrates steps of the invention.
Figure 11:
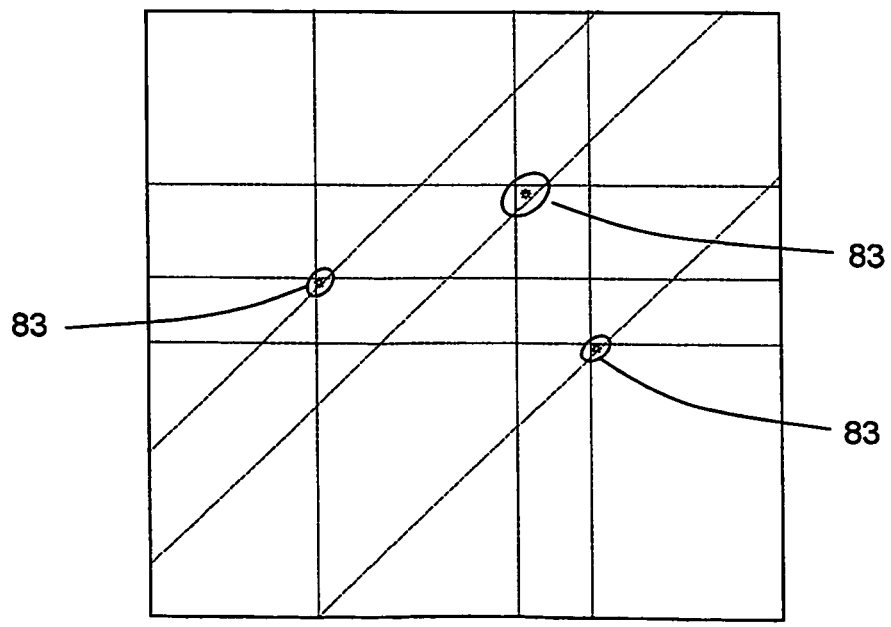
FIG. 11 illustrates centroids, of the N=3 densest closest-point sets used to represent the actual 2D locations of the fiducial markers in the scan plane.

Referring now to FIG. 10, the step of determining the 3D coordinates of fiducial markers also includes estimating the closest-point set density and centroid. The mean separating distance was computed for each closest-point set by averaging the distances between the reference point and the other members of the set. A closest-point set's relative density was estimated by comparing the mean separating distances. Each set point was ranked according to its mean separating distance at 82. The centroids, shown at 83 in FIG. 11, of the N=3 densest (smallest mean separating distance) closest-point sets were used to represent the actual 2D locations of the fiducial markers in the scan plane at 84.

Figures 12, 13:
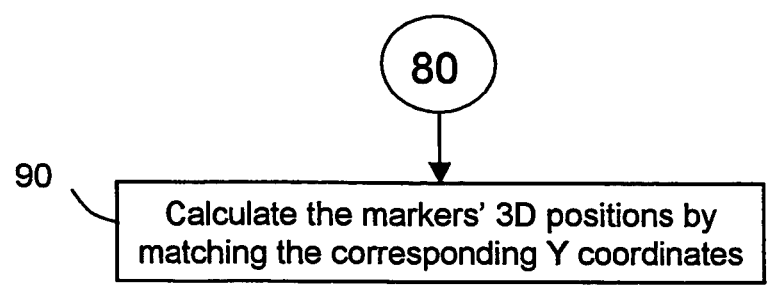
FIG. 12 illustrates steps of the invention.
FIG. 13 illustrates the matching of the corresponding Y coordinates of the fiducial markers from axial (X-Y plane) and sagittal (Y-Z plane) scans in accordance with the invention.
Figure 14:
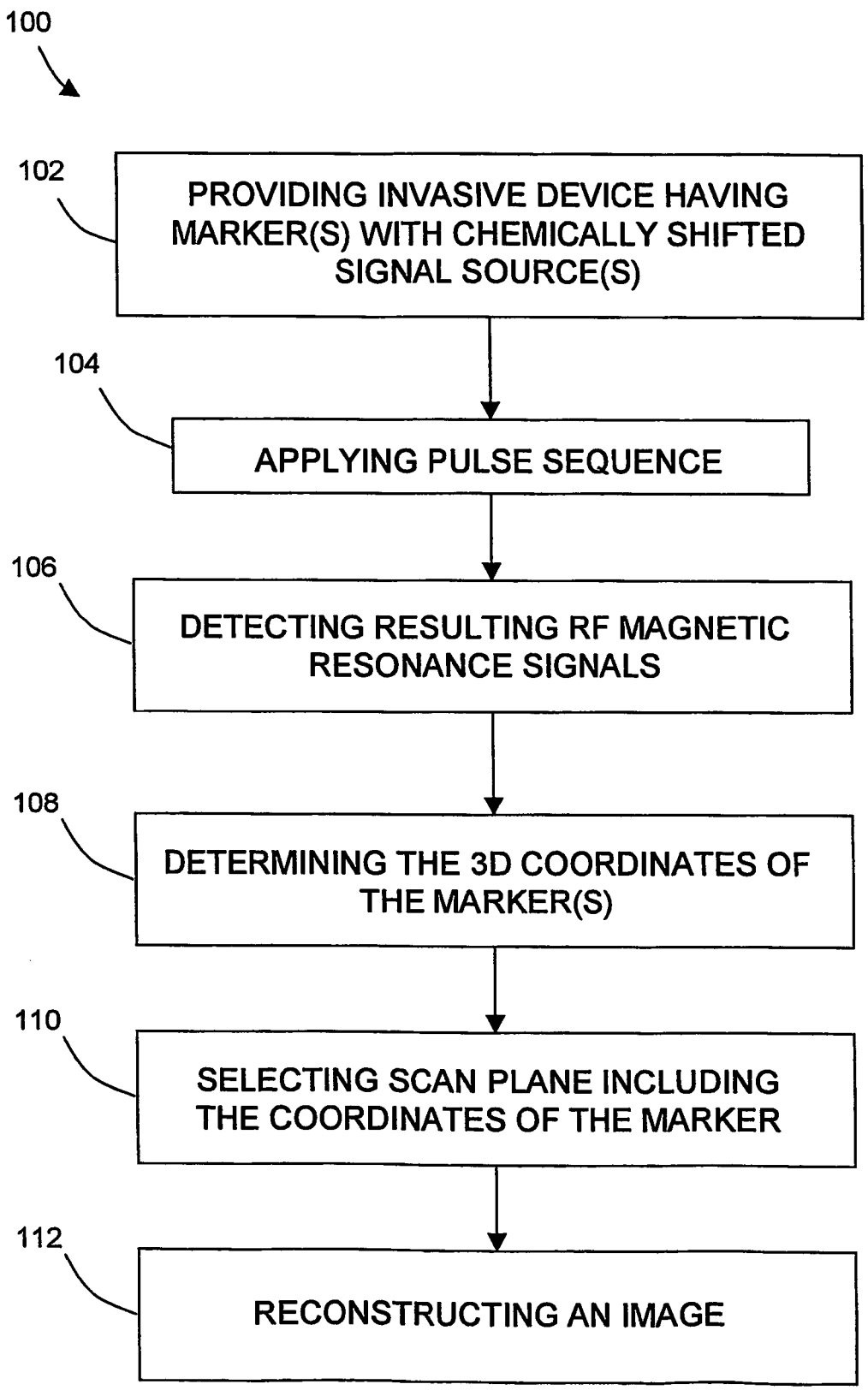
FIG. 14 illustrates a method for selecting a scan plane in accordance with the invention.

Referring now to FIG. 12, the step of determining the 3D coordinates of fiducial markers also includes obtaining the 3D coordinates using orthogonal scan planes shown generally at 90. A linear least squares routine was used to match the corresponding Y coordinates of the fiducial markers from axial (X-Y plane) and sagittal (Y-Z plane) scans as shown in FIG. 13. The resulting three-dimensional position of each fiducial marker 13 included the average of the two Y coordinates, and the X and Z coordinates that were associated with the marker's 2D position in each scan plane.

The method 10 also includes reconstructing an image from the detected signals, shown at 20 in FIG. 1, in any suitable know manner to produce an image of the marker for use in tracking the device. The radial MPSSFP images were reconstructed from 256 projections, though any suitable number can be used.

In accordance with a yet another aspect of the invention, a method for selecting scan planes in MRI is provided as shown generally at 100. The method includes providing an invasive device including a marker having a chemically shifted signal source with a resonant frequency different from the chemical species of a subject to be imaged at 102. The device can be any suitable invasive device as described above having one or more markers as described above.

The method also includes applying a pulse sequence at 104 similar to the pulse sequence described above, and detecting the resulting RF magnetic resonance signals at 106. The method also includes determining the 3D coordinates of the marker at 108 in any suitable manner, such as for example that described above. The method also includes selecting one or more scan planes which include the 3D coordinates of the marker or markers at 110. The method can also include reconstructing an image having the marker contrasted from the subject at 112.

The invention improves tracking of markers 13 based on chemical shift which can be used to track and guide an invasive device D when attached thereto. The markers 13 can be disposed on, in or about the invasive device D to provide spatial localization of the markers which can be used for device tracking and acquisition of scan plans. With the invention the position and orientation of the interventional device D is less constrained as compared to other known fiducial marker tracking methods.

A radial missing pulse steady state free precession (MPSSFP) sequence can be used to provide marker contrast necessary for 3D localization of the markers and automatic scan plane selection in interventional MRI procedures, although other suitable known pulse sequences can be used. The marker contrast provided by the radial MPSSFP sequence allows the 3D coordinates to be analytically determined by existing localization algorithms. The radial MPSSFP was established to match the signal characteristics and relaxation parameters of the concentrated acetic acid/Gd-contrast solution.

The invention has been described with reference to preferred embodiments. Obviously, modifications and alterations will occur to others upon reading and understanding the preceding specification. It is intended that the invention be construed as including all such modifications and alterations insofar as they come within the scope of the appended claims or the equivalents thereof.

What is claimed is:

1. A method for spatial localization of an invasive device in Magnetic Resonance Imaging (MRI) comprising:
    placing, in a subject to be imaged, an invasive device including at least three markers distributed as point sources defining a plane and having a chemically shifted signal source with a resonant frequency different from the chemical species of the subject to be imaged;
    applying a pulse sequence;
    detecting the resulting RF magnetic resonance signals; and
    determining the 3D coordinates of the at least three markers.

2. The method for spatial localization defined in claim 1, comprising selecting scan planes for MR imaging.

3. The method for spatial localization defined in claim 2, where the scan planes include the at least three markers.

4. The method defined in claim 1, comprising acquiring scan volumes containing the at least three markers.

5. The method for spatial localization defined in claim 1, comprising generating marker only projections for tracking the device during its movement in the subject.

6. The method for spatial localization defined in claim 1, where the at least three markers is doped to improve the signal received.

7. The method for spatial localization defined in claim 1, where the at least three markers includes acetic acid.

8. The method for spatial localization defined in claim 1, where the at least three markers are blood-safe.

9. The method for spatial localization defined in claim 8, where the at least three markers include fluorinated compounds.

10. The method for spatial localization defined in claim 9, where the at least three markers include perflourocarbon.

11. The method for spatial localization defined in claim 1, where the at least three markers are arranged as a line source.

12. The method for spatial localization defined in claim 1, comprising using the plane to indicate the orientation of the device.

13. The method for spatial localization defined in claim 1, where applying a pulse sequence includes applying a radial 2-pulse missing pulse steady state sequence.

14. The method for spatial localization defined in claim 13, where the radial 2-pulse missing pulse steady state sequence includes applying a slice-selective pulse and a chemical shift selective pulse.

15. The method for spatial localization defined in claim 13, where the radial 2-pulse missing pulse steady state sequence includes TR/TE/FA=30 ms/20 ms/135°.

16. The method for spatial localization defined in claim 1, where applying a pulse sequence includes applying a dephasing pulse.

17. The method for spatial localization defined in claim 1, comprising reconstructing an image from the detected signals to acquire an image having the at least three markers contrasted from the subject.

18. The method defined in claim 1, comprising generating a limited set of 1D radial projections in two orthogonal scan planes.

19. The method defined in claim 18, where the determining includes analyzing the 1D projections from the pulse sequence to identify the 3D coordinates of the at least three markers.

20. The method defined in claim 19, where the determining includes: converting the raw MRI projection data into the spatial domain by applying a 1D-FFT; and finding the location of the at least three markers within each projection.

21. The method defined in claim 20, where the determining includes locating the intersections created by backprojecting the at least three markers signal peaks found in each projection into the scan plane.

22. The method defined in claim 21, where the determining includes designating a subset of the intersection points as reference points and forming a "closest-point set" around the reference points.

23. The method defined in claim 22, where the determining includes representing the 2D locations of the at least three markers in the scan plane using the centroids of the densest "closest-point sets".

24. The method defined in claim 23, where the determining includes finding the XY and YZ coordinates separately.

25. The method defined in claim 24, where the determining includes matching the corresponding Y coordinates to assign the 3D locations to each marker.

26. The method defined in claim 1, including tracking the invasive device.

* * * * *

UNITED STATES PATENT AND TRADEMARK OFFICE
CERTIFICATE OF CORRECTION

PATENT NO. : 9,031,634 B2
APPLICATION NO. : 10/514307
DATED : May 12, 2015
INVENTOR(S) : Christopher Flask et al.

Page 1 of 1

It is certified that error appears in the above-identified patent and that said Letters Patent is hereby corrected as shown below:

In the Specification:

In column 1, line 16, delete "incisions resulting" and insert --incisions, resulting--.

In column 1, line 29, delete "room which" and insert --room, which--.

In column 1, line 49, delete "markers which" and insert --markers, which--.

In column 1, line 62, delete "signals, determining" and insert --signals, and determining--.

In column 2, line 19, delete "include" and insert --includes--.

In column 2, line 49, delete "centroids, of" and insert --centroids of--.

In column 3, line 16, delete "ppm))" and insert --ppm)--.

In column 3, line 36, delete "points" and insert --point--.

In column 4, line 41, delete "all of markers" and insert --all marker--.

In column 5, line 23, delete "Here m" and insert --Here, m--.

In column 6, line 5, delete "know" and insert --known--.

In column 6, line 33, delete "tion the" and insert --tion, the--.

In the Claims:

In column 7, line 9, delete "is" and insert --are--.

In column 7, line 12, delete "includes" and insert --include--.

Signed and Sealed this
Twenty-first Day of June, 2016

Michelle K. Lee
*Director of the United States Patent and Trademark Office*